(12) United States Patent
D'Andrea

(10) Patent No.: US 10,086,213 B2
(45) Date of Patent: Oct. 2, 2018

(54) MOBILE GYNECOLOGICAL BALLOON DEVICES AND METHODS

(71) Applicant: Mark A. D'Andrea, Houston, TX (US)

(72) Inventor: Mark A. D'Andrea, Houston, TX (US)

( * ) Notice: Subject to any disclaimer, the term of this patent is extended or adjusted under 35 U.S.C. 154(b) by 286 days.

(21) Appl. No.: 14/693,986

(22) Filed: Apr. 23, 2015

(65) Prior Publication Data

US 2016/0310759 A1    Oct. 27, 2016

(51) Int. Cl.
*A61N 5/10*    (2006.01)

(52) U.S. Cl.
CPC .... *A61N 5/1016* (2013.01); *A61N 2005/1008* (2013.01)

(58) Field of Classification Search
CPC .................. A61N 5/1016; A61N 2005/1008
See application file for complete search history.

(56) References Cited

U.S. PATENT DOCUMENTS

| | | |
|---|---|---|
| 899,477 A | 9/1908 | Williams |
| 3,060,924 A | 10/1962 | Rush |
| 3,173,418 A | 3/1965 | Baran |
| 3,435,826 A | 4/1969 | Fogarty |
| 3,467,101 A | 9/1969 | Fogarty et al. |
| 3,543,744 A | 12/1970 | LePar |
| 3,841,304 A | 10/1974 | Jones |
| 3,861,380 A | 1/1975 | Chassagne et al. |
| 4,263,917 A | 4/1981 | Moss |
| 4,292,960 A | 10/1981 | Paglione |

(Continued)

FOREIGN PATENT DOCUMENTS

| | | |
|---|---|---|
| CA | 0669316 | 12/1964 |
| EP | 1 568397 A1 | 8/2005 |

(Continued)

OTHER PUBLICATIONS

The International Search Report and the Written Opinion of the International Searching Authority, PCT/US2014/020507, dated Jun. 2014.

(Continued)

*Primary Examiner* — Kaylee Wilson
(74) *Attorney, Agent, or Firm* — Cook Alex Ltd.

(57) ABSTRACT

Brachytherapy oncology treatment systems and methods are provided. One such system and method employs a catheter or tandem and a mobile balloon device having an enclosed inner volume and an internal surface with an internal perimeter size larger than the external surface perimeter size and adequate to allow sliding longitudinal movement between the catheter or tandem and the mobile balloon device. The mobile balloon device has a radiation dose delivery tube that is at or moves by inflation to a strategic radiation dose delivery location for brachytherapy. An embodiment allows for a multi-part catheter or tandem having a detachable distal section suitable for retaining within a body cavity such as the uterus, both during radiation treatment and during recovery time between radiation treatments. This distal portion can be intended for single-patient use and be disposed of after completion of a radiation treatment session having multiple radiation dose treatment times. One or both of real time in vivo detection and monitoring and hyperthermia features can be included.

26 Claims, 7 Drawing Sheets

(56) References Cited

U.S. PATENT DOCUMENTS

| | | | |
|---|---|---|---|
| 4,294,264 A | 10/1981 | Fishell et al. | |
| 4,318,410 A | 3/1982 | Chin | |
| 4,323,055 A | 4/1982 | Kublatowicz | |
| 4,349,033 A | 9/1982 | Fden | |
| 4,434,789 A | 3/1984 | Kumar | |
| 4,448,198 A | 5/1984 | Turner | |
| 4,471,779 A | 9/1984 | Antoshkiw et al. | |
| 4,554,909 A * | 11/1985 | Pino y Torres | A61M 31/005 600/6 |
| 4,631,415 A | 12/1986 | Sauerwein et al. | |
| 4,733,653 A | 3/1988 | Leung | |
| 4,744,366 A | 5/1988 | Jang | |
| 4,775,362 A | 10/1988 | Kronner | |
| 4,798,215 A | 1/1989 | Turner | |
| 4,813,934 A | 3/1989 | Engelson et al. | |
| 4,861,520 A | 8/1989 | van't Hooft et al. | |
| 4,881,937 A | 11/1989 | van't Hooft et al. | |
| 4,881,938 A | 11/1989 | van't Hooft et al. | |
| 4,897,076 A | 1/1990 | Puthawala et al. | |
| 4,919,651 A | 4/1990 | Doane | |
| 4,947,842 A | 8/1990 | Marchosky et al. | |
| 4,967,765 A | 11/1990 | Turner et al. | |
| 4,969,863 A | 11/1990 | van't Hooft et al. | |
| 5,012,357 A | 4/1991 | Schoeppel et al. | |
| 5,019,042 A | 5/1991 | Sahota | |
| 5,049,132 A | 9/1991 | Schaffer et al. | |
| 5,090,043 A | 2/1992 | Parker et al. | |
| 5,106,360 A | 4/1992 | Ishiwara et al. | |
| 5,122,113 A | 6/1992 | Hattler | |
| 5,135,494 A | 8/1992 | Engelson et al. | |
| 5,147,300 A | 9/1992 | Robinson et al. | |
| 5,249,585 A | 10/1993 | Turner et al. | |
| 5,306,271 A | 4/1994 | Zinreich et al. | |
| 5,342,305 A | 8/1994 | Shonk | |
| 5,411,466 A | 5/1995 | Hess | |
| 5,429,582 A | 7/1995 | Williams | |
| 5,503,613 A | 4/1996 | Weinberger | |
| 5,520,646 A | 5/1996 | D'Andrea | |
| 5,562,594 A | 10/1996 | Weeks | |
| 5,653,683 A | 8/1997 | D'Andrea | |
| 5,720,717 A | 2/1998 | D'Andrea | |
| 5,902,251 A | 5/1999 | vanHooydonk | |
| 5,913,813 A | 6/1999 | Williams et al. | |
| 6,017,322 A | 1/2000 | Snoke et al. | |
| 6,083,148 A | 7/2000 | Williams | |
| 6,312,375 B1 | 11/2001 | Montebello et al. | |
| 6,413,204 B1 | 7/2002 | Winkler et al. | |
| 6,482,142 B1 | 11/2002 | Winkler et al. | |
| 6,679,860 B2 | 1/2004 | Stiger | |
| 6,699,171 B2 | 3/2004 | Harmon | |
| 6,746,465 B2 | 6/2004 | Diederich et al. | |
| 6,866,624 B2 | 3/2005 | Chomenky et al. | |
| 7,447,550 B2 | 11/2008 | Eggers et al. | |
| 7,476,235 B2 | 1/2009 | Diederich | |
| 7,534,202 B2 | 5/2009 | Eng | |
| 7,556,596 B2 | 7/2009 | Mourtada et al. | |
| 7,651,458 B2 | 1/2010 | Mourtada et al. | |
| 7,666,130 B2 | 2/2010 | Mick | |
| 8,033,979 B2 | 10/2011 | Mick | |
| 8,423,152 B2 | 4/2013 | Turner et al. | |
| 8,500,771 B2 | 8/2013 | Isham | |
| 8,636,637 B2 | 1/2014 | Lubock et al. | |
| 8,979,725 B2 | 3/2015 | D'Andrea | |
| 2002/0111560 A1 | 8/2002 | Kokate et al. | |
| 2003/0153803 A1 | 8/2003 | Harmon | |
| 2004/0147811 A1 | 7/2004 | Diederich et al. | |
| 2005/0059965 A1 * | 3/2005 | Eberl | A61B 18/1492 606/41 |
| 2005/0251235 A1 | 11/2005 | Schlorff et al. | |
| 2006/0030914 A1 | 2/2006 | Eggers et al. | |
| 2006/0116546 A1 | 6/2006 | Eng | |
| 2006/0205992 A1 | 9/2006 | Lubock et al. | |
| 2008/0064916 A1 | 3/2008 | Mick | |
| 2008/0086050 A1 | 4/2008 | Miwic et al. | |
| 2008/0228063 A1 | 9/2008 | Turner et al. | |
| 2009/0299327 A1 * | 12/2009 | Tilson | A61B 17/8816 604/500 |
| 2010/0100092 A1 | 4/2010 | Turner et al. | |
| 2010/0145132 A1 | 6/2010 | Isham | |
| 2011/0182880 A1 | 7/2011 | Von Stein et al. | |
| 2011/0200526 A1 | 8/2011 | Parsal et al. | |
| 2011/0224477 A1 | 9/2011 | Issels | |
| 2012/0123188 A1 | 5/2012 | Rahimian | |
| 2012/0172651 A1 | 7/2012 | Cutrer | |
| 2012/0215053 A1 | 8/2012 | Gim | |
| 2013/0109906 A1 * | 5/2013 | Valoir | 600/3 |
| 2013/0177566 A1 | 7/2013 | Ruben et al. | |
| 2013/0261368 A1 | 10/2013 | Schwartz | |
| 2013/0317276 A1 * | 11/2013 | D'Andrea | A61N 5/1016 600/2 |
| 2014/0257013 A1 | 9/2014 | D'Andrea | |
| 2014/0257088 A1 | 9/2014 | D'Andrea | |
| 2014/0275712 A1 | 9/2014 | D'Andrea | |
| 2015/0157878 A1 | 6/2015 | D'Andrea | |

FOREIGN PATENT DOCUMENTS

| | | |
|---|---|---|
| GB | 197805 | 5/1978 |
| WO | WO 02/102451 A1 | 12/2002 |

OTHER PUBLICATIONS

The International Search Report and the Written Opinion, of PCT/US2013/042165, dated Aug. 21, 2013.

Horton, John et al., LDR Intracavitary Brachytherapy Applicators, UT MD Anderson Cancer Centerintracavitary Brachytherapy, 2005.

http://www.cancer.org/Treatment/TreatmentsandSide Effects/TreatmentTypes/hyperthermia, Downloaded May 2, 2012.

Research Spotlight, Eos, vol. 92, No. 33, Aug. 16, 2011.

Zhu, Timothy C., Diode Dosimetry for Megavoltage ElectronandPhoton Beams, Dept. of Radiation Oncology, U. ofPennsylvania, Philadelphia, PA Jun. 24, 2009.

Dutta, Pinaki, MD et al., How isradiation therapy given?, OncoLink Cancer Resources, www.oncolink.org/treatmentiarticle, Downloaded Oct. 28, 2011.

http://vantageoncology.com/centers2006/html/body/treatment/wildomar, High-Dose Rate Brachytherapy (HDR) TandemandOvoice Implant, WildomarRadiationTherapyCentr, Download Oct. 31.

www.americanbrachytherapy.org/aboutBrachytherapy, What is Brachytherapy?, American Brachytherapy Society, Downloaded Nov. 4, 2009.

Section III: Disease Sites, Chapter 22: Uterine Cervix. textbook p. 657-659, circa 2001.

Corrao, Anita, MS, CMA, DABRE, A comparison of APBI brachytherapy techniques: MammoSite . . . , Lifespan, Providence, RI 2010.

MicroSelectron—body site applicator solutions, Oncoselect by Nucletron, circa Mar. 2010.

BSD-500 Hyperthermia System brochure, BSD Medical Corporation, 2007.

BSD-2000 Hyperthermia System, BSD Medical Corporation, 2010.

E-Z EM, Inc., "Protect Delicate Pelvic Tissues with E-Z-EM's Shadow-Form TM Marks for Radiation Oncology", E-Z-EM Product Update, 1993.

Nucletron Corporation, "The Nucletron Difference—High Dose Rate Brachytherapy", brochure through p. 9, 1992.

Omnitron, "The New Generation of High Dose Rate Remote Afterloaders", brochure, Omnitron International Inc., 1991.

"Brachytherapy Interstitial & Intracavitary Applicators & Accessories", catalog 9301 (Jan. 1993), Mick Radio—Nuclear Instruments, Inc.

* cited by examiner

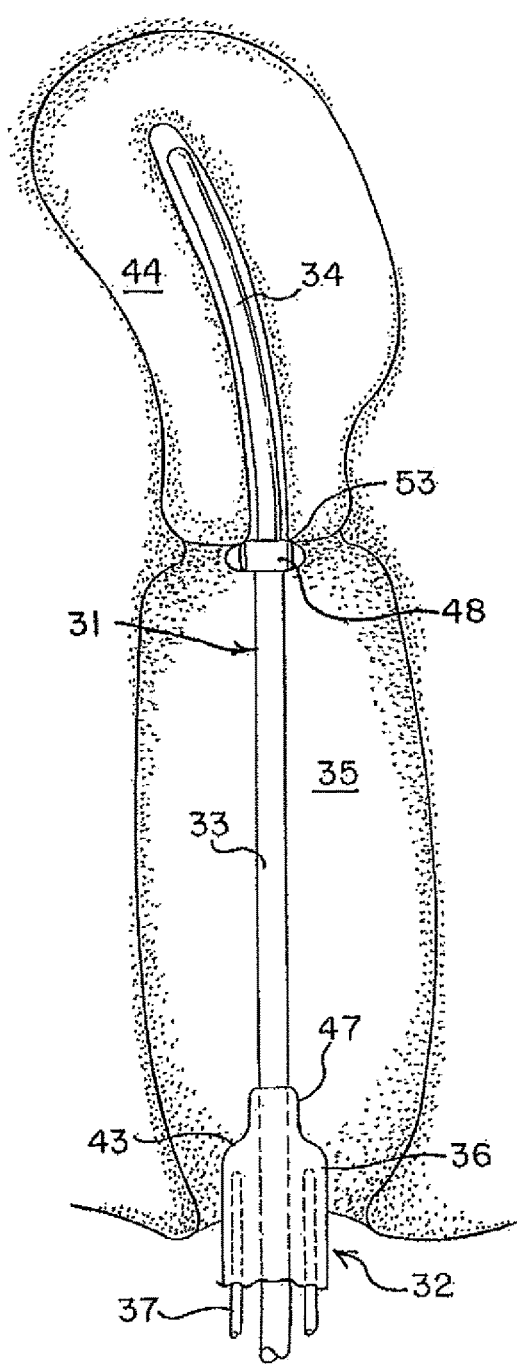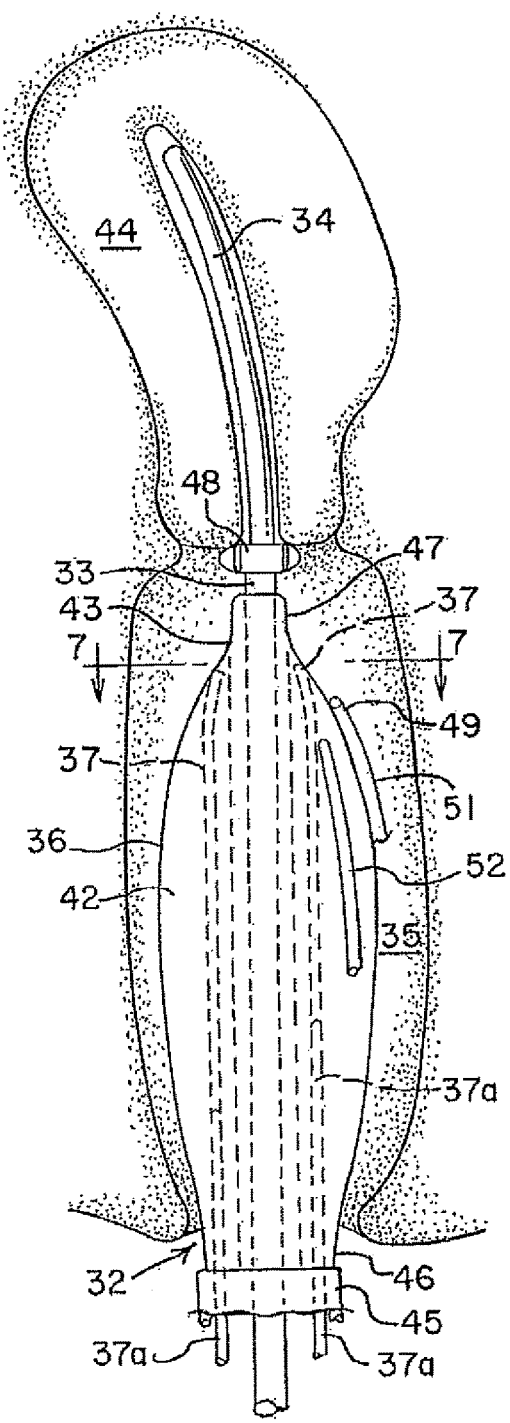

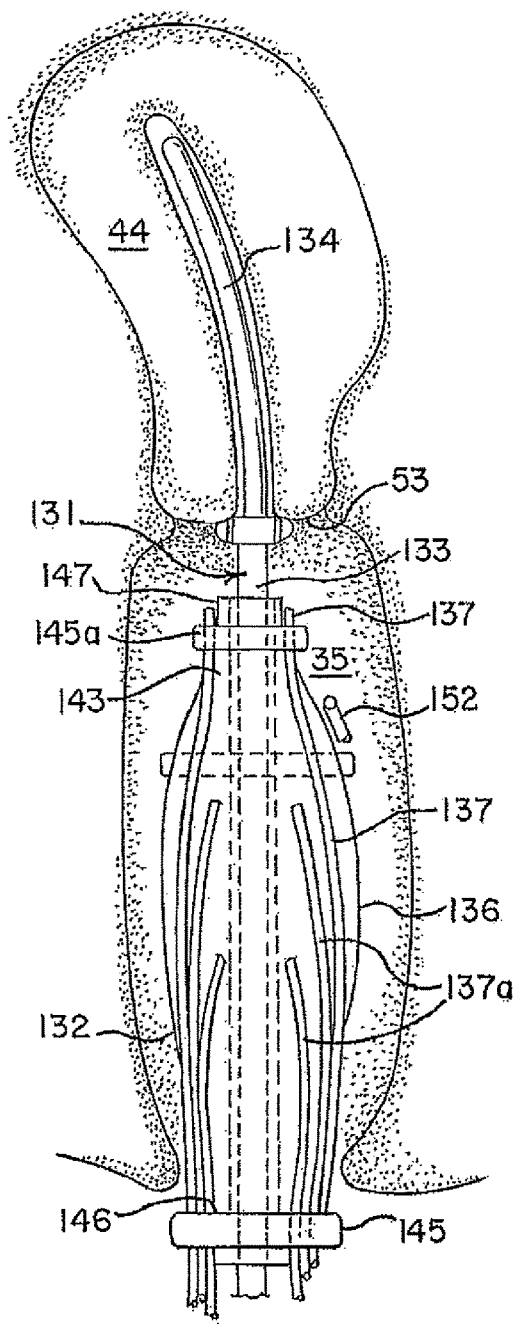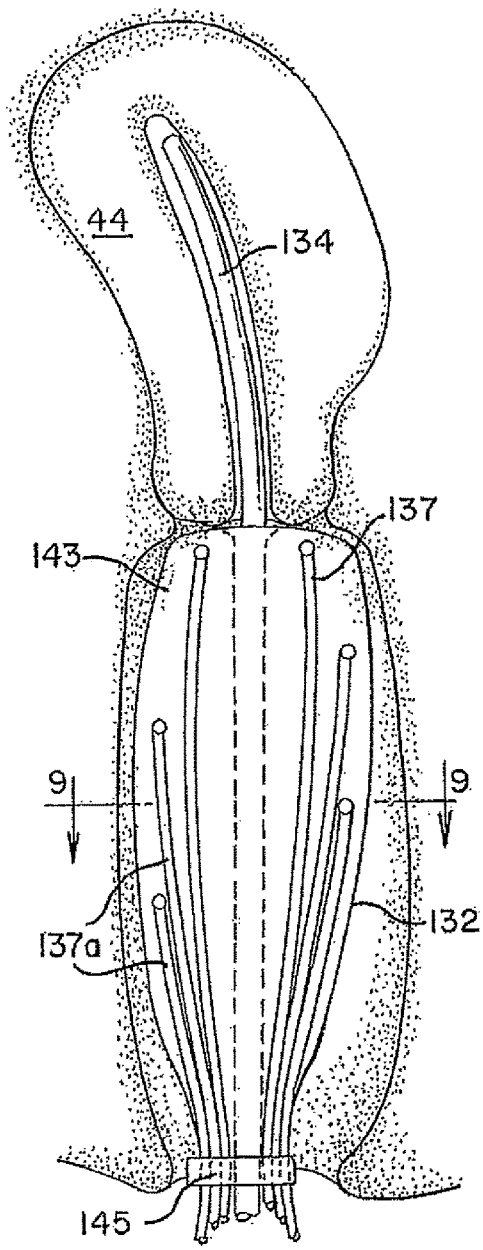

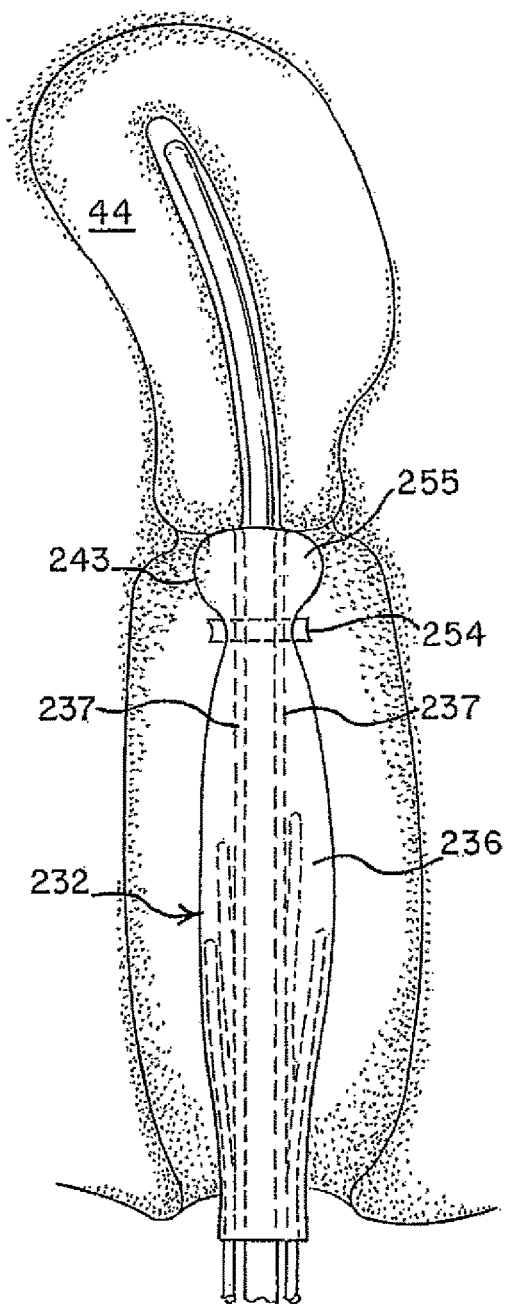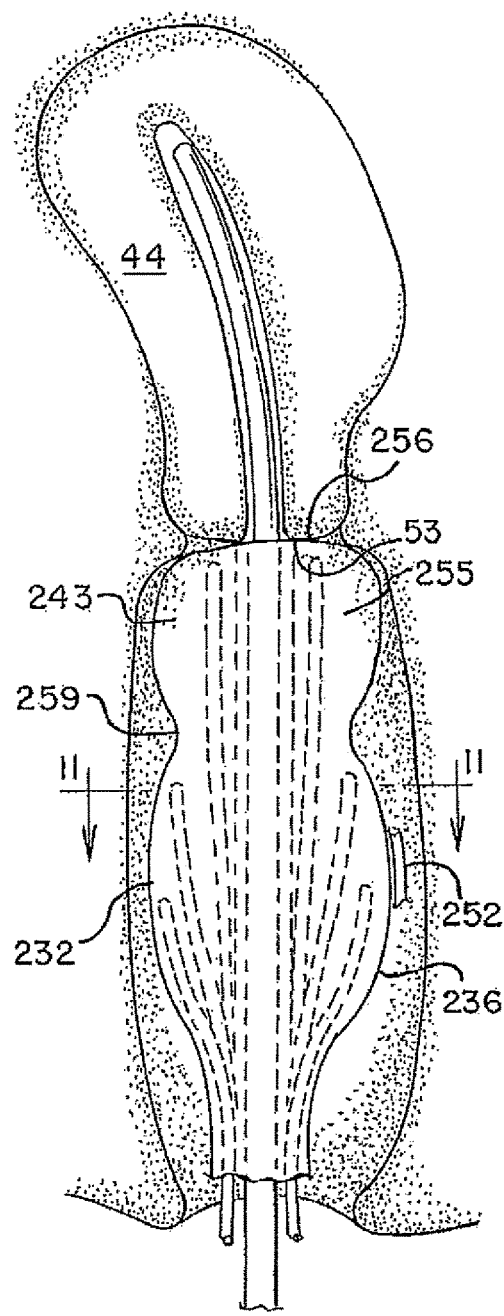

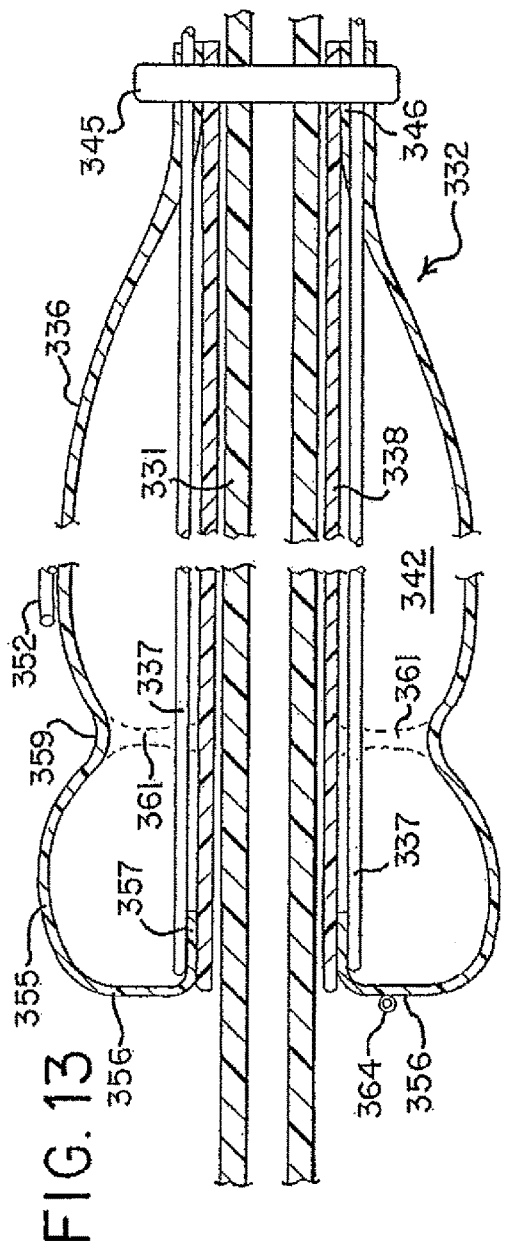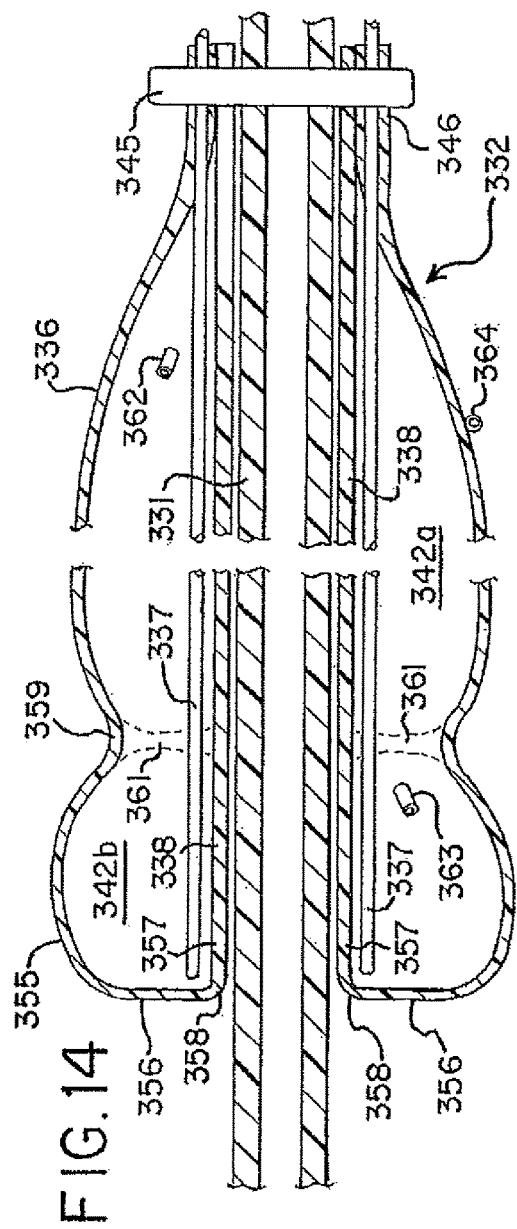

MOBILE GYNECOLOGICAL BALLOON DEVICES AND METHODS

BACKGROUND

Field of the Disclosure

The present subject matter relates to mobile gynecological and intrauterine devices and methods, particularly as used for brachytherapy and in the context of tandem and ovoid implantation systems and methods employing same. More particularly, the present subject matter relates to such systems wherein a mobile balloon device is positioned with respect to a longitudinally extending component, such as a catheter or a gynecological tandem type of device, the mobile balloon having radiation dose delivery components.

Description of Related Art

Numerous devices and methods are known for intrauterine brachytherapy use. Many of these incorporate a tandem delivery tube and an ovoid or ovoids, at least one of which is associated with a colpostat function. Often, dual ovoid colpostats are included and generally flank the tandem delivery tube. With this general approach, multiple delivery paths are available for treatment of different intrauterine locations.

Radiation oncology intracavitary brachytherapy practitioners and researchers have developed various systems. In the Manchester system, for example, a tandem and two ovoids are available in differing diameter sizes. In the Fletcher system, the ovoid colpostats have internal shielding, and polymer caps can be added to increase diameter. Different styles of tandems are available, having different curvatures and/or lengths, and a yoke attaches the tandem and ovoids together and facilitates maintaining proper positioning during treatment. Other systems include the Madison system, the Paris system and the Stockholm system. Typically in each of these systems, the tandem is inserted first, followed by the ovoids or other treatment components or devices. Typical treatment patterns or regimens follow multiple doses, and thus multiple intrauterine insertions and removals of the equipment are spaced apart in time by non-treatment intervals that vary depending upon the oncology protocol. Those application or treatment times typically vary between about five to twenty minutes. Usually the total treatment time is two or three days, with multiple treatments and non-treatment intervals proceeding during this timeframe.

Procedures for treating uterine or cervical carcinoma with tandem and ovoid systems and implant procedures typically follow a protocol calling for a series of three to seven implants, such as when following high dose rate (HDR) brachytherapy. At times, the oncologist may choose to use a low dose rate (LDR) brachytherapy regimen, typically based on cesium delivery as $^{137}$Cs. For HDR brachytherapy regimens $^{192}$Ir is frequently used because of its high specific activity. Other isotopes are available and used as warranted. The degree of treatment is measured in terms of units of radiation exposure (in roentgens or Gray or Gy) that are prescribed at specific points, termed A and B, within the pelvis including noting locations keyed to the center of the uterine canal, the mucous membrane of the lateral fornix in the plane of the uterus, the paracervical triangle, and the regional (Obturator) lymph nodes. An objective is to provide reasonably constant and predictable dose rates at each location, as applied by the isotopes of the tandem and ovoid system. Details in this regard are generally are known to the medical professional.

Accordingly, it is clear that intracavitary brachytherapy such as that used in treating vaginal, uterine and cervical cancers needs to be exacting and specific in dose rates, durations and radiation target locations. Oncology treatment systems and methods such as tandem and ovoid combinations demand dosage rate and location precision during intrauterine brachytherapy. In addition, the closeness of tissues not intended to be irradiated should be taken into consideration. For example, it is important to minimize, if not eliminate, radiation exposure to the bladder and rectum. Generally, tandem and ovoid positions are noted on X-ray images in order to ensure intended placement and to allow the medical physicist or professional to generate a radiation treatment plan specific for this placement and for the particular anatomy and disease location and severity for the particular patient and for this treatment event.

It will be appreciated that tandem colpostat delivery systems, including ovoids or not, can be used in brachytherapy that is applied manually or remotely using remote afterloading systems. In remote afterloading systems, the radioactive materials are delivered from a safely contained source by way of hollow tubes to hollow portions of the tandem and/or ovoid components. Radioactive material can be in the form of wires or seeds. In such systems, the radioactive material is delivered via remote control, such as by operation of a motor, after the medical professionals all are removed from the treatment room. Such remote delivery equipment moves the radioactive dose into the applicator (such as a tandem, an ovoid or other colpostat) previously positioned within the body cavity.

SUMMARY

There are several aspects of the present subject matter that may be embodied separately or together in the systems, devices and methods described herein and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect or embodiment, a brachytherapy catheter and mobile balloon device system is provided in which the catheter has a distal section and a proximal section having a longitudinally oriented external surface of a given perimeter size. A mobile balloon device includes an inflatable balloon having a proximal end portion with a proximal leg, and a distal end portion with a distal leg, and the mobile balloon device has an enclosed inner volume structured to receive and securely confine an inflation fluid, the enclosed inner volume being defined partially or fully by the inflatable balloon. The mobile balloon device further includes an internal surface having an internal surface perimeter size larger than the catheter external surface perimeter size and adequate to allow sliding longitudinal movement between the catheter and the mobile balloon device. The mobile balloon device further includes at least one radiation dose delivery tube that is positioned, for example by inflation of the balloon with the inflation fluid, to a strategic radiation dose delivery location for brachytherapy.

In yet another aspect or embodiment, a brachytherapy catheter such as a tandem and mobile balloon device system is provided in which the catheter has a distal section and a proximal section having a longitudinally oriented external surface of a given perimeter size. A mobile balloon device includes an inflatable balloon having a proximal end portion with a proximal leg, a distal end portion with a distal leg, and the mobile balloon device has an enclosed inner volume structured to receive and securely confine an inflation fluid. The mobile balloon device further includes an internal surface or a portion of the inflatable balloon defining a further portion of the enclosed inner volume, the internal surface having an internal surface perimeter size larger than the catheter external surface perimeter size and adequate to allow sliding longitudinal movement between the catheter and the mobile balloon device. The mobile balloon device further includes at least one radiation dose delivery tube that is positioned within the enclosed inner volume of the inflatable balloon and is manipulatable by the medical professional to position, for example by inflation of the balloon with an inflation fluid, to a strategic radiation dose delivery location for brachytherapy.

In a further aspect or embodiment, a brachytherapy catheter such as a tandem and mobile balloon device system in which the catheter has a distal section and a proximal section having a longitudinally oriented external surface of a given perimeter size. A mobile balloon device includes an inflatable balloon having a proximal end portion with a proximal leg, a distal end portion with a distal leg, and the mobile balloon device has an enclosed inner volume structured to receive and securely confine an inflation fluid, the enclosed inner volume being defined by the inflatable balloon and by an internal surface defining a further portion of the enclosed inner volume, the internal surface having an internal surface perimeter size larger than the catheter external surface perimeter size and adequate to allow sliding longitudinal movement between the catheter and the mobile balloon device. The mobile balloon device further includes at least one radiation dose delivery tube that is positioned within the inflatable balloon and is manipulatable by the medical professional to position, for example by inflation of the balloon with an inflation fluid, to a strategic radiation dose delivery location for brachytherapy.

Another aspect or embodiment concerns a brachytherapy catheter such as a tandem and mobile balloon device system in which the catheter has a distal section and a proximal section having a longitudinally oriented external surface of a given perimeter size. A mobile balloon device includes an inflatable balloon having a wall with a proximal leg, a distal end portion with a distal leg, and the mobile balloon device has an enclosed inner volume structured to receive and securely confine an inflation fluid, the enclosed inner volume being defined fully or partially by the inflatable balloon. The mobile balloon device or a portion of the inflatable balloon further includes an internal surface defining a further portion of the enclosed inner volume, the internal surface having an internal surface perimeter size larger than the catheter external surface perimeter size and adequate to allow sliding longitudinal movement between the catheter and the mobile balloon device. The mobile balloon device further includes at least one radiation dose delivery tube that is positioned within the inflatable balloon in association with a plug at the proximal end of the mobile balloon device through which the tube passes, and the plug is manipulatable by the medical professional to position, for example by inflation of the balloon with an inflation fluid, to a strategic radiation dose delivery location for brachytherapy.

In a further aspect or embodiment, a brachytherapy catheter such as a tandem and mobile balloon device system is provided in which the catheter has a distal section and a proximal section having a longitudinally oriented external surface of a given perimeter size. A mobile balloon device includes an inflatable balloon having a wall with a known wall thickness, a proximal end portion with a proximal leg, and a distal end portion with a distal leg, and the mobile balloon device has an enclosed inner volume and an internal surface structured to receive and securely confine an inflation fluid, the internal surface having an internal surface perimeter size larger than the catheter external surface perimeter size and adequate to allow sliding longitudinal movement between the catheter and the mobile balloon device. The mobile balloon device further includes at least one radiation dose delivery tube that is positioned outside of and generally along the inflatable balloon and is manipulatable by the medical professional to position, for example by inflation of the balloon with an inflation fluid, to a strategic radiation dose delivery location for brachytherapy.

According to another embodiment or aspect, a brachytherapy catheter such as a tandem and mobile balloon device system is provided in which a tandem has a distal section and a proximal section having a longitudinally oriented external surface of a given perimeter size. A mobile balloon device includes an inflatable balloon having a wall with a proximal leg, a distal end portion with a distal leg, and the mobile balloon device has an enclosed inner volume structured to receive and securely confine an inflation fluid and an internal surface and an internal surface perimeter size larger than the catheter external surface perimeter size and adequate to allow sliding longitudinal movement between the catheter and the mobile balloon device. The mobile balloon device further includes at least one radiation dose delivery tube that is positioned outside of and generally along the inflatable balloon with a collar at the distal end area, the proximal end area, or both, of the inflatable balloon, the delivery tube being manipulatable by the medical professional to position, for example by inflation of the balloon with an inflation fluid, to a strategic radiation dose delivery location for brachytherapy.

In a further embodiment or aspect, a brachytherapy catheter such as a tandem and mobile balloon device system is provided in which a tandem has a distal section and a proximal section having a longitudinally oriented external surface of a given perimeter size. A mobile balloon device includes an inflatable balloon having a wall with a known wall thickness, a proximal end portion with a proximal leg, and a distal end portion with a distal leg, and the mobile balloon device has an enclosed inner volume structured to receive and securely confine an inflation fluid, the enclosed inner volume being defined fully or partially by the inflatable balloon. The mobile balloon device further includes an internal surface or a portion of the inflatable balloon defining a further portion of the enclosed inner volume, the internal surface having an internal surface perimeter size larger than the tandem external surface perimeter size and adequate to allow sliding longitudinal movement between the tandem and the mobile balloon device. The mobile balloon device further includes at least one radiation dose delivery tube that is positioned within the wall thickness of the inflatable balloon and is manipulatable by the medical professional to position, for example by inflation of the balloon with an inflation fluid, to a strategic radiation dose delivery location for brachytherapy.

In a further embodiment or aspect, a brachytherapy tandem and mobile balloon device system is provided in which a tandem has a distal section and a proximal section having a longitudinally oriented external surface of a given perimeter size. A mobile balloon device includes an inflatable balloon having a wall with a known wall thickness, a proximal end portion with a proximal leg, and a distal end portion with a distal leg, and the mobile balloon device has an enclosed inner volume and an internal surface structured to receive and securely confine an inflation fluid, the internal surface having an internal surface perimeter size larger than the catheter external surface perimeter size and adequate to allow sliding longitudinal movement between the catheter and the mobile balloon device. The mobile balloon device further includes at least one radiation dose delivery tube that extends to a distal end location of the mobile balloon device system, thereby directing the radiation delivery to a patient's cervix, including upon inflation of the balloon with the inflation fluid, to a strategic radiation dose delivery location for cervix brachytherapy.

An additional embodiment or aspect concerns a brachytherapy catheter such as a tandem and mobile balloon device system in which the catheter has a distal section and a proximal section having a longitudinally oriented external surface of a given perimeter size. A mobile balloon device includes an inflatable balloon having a proximal end portion with a proximal leg, a distal end portion with a distal leg, and the mobile balloon device has an enclosed inner volume structured to receive and securely confine an inflation fluid, the enclosed inner volume being defined fully or partially by the inflatable balloon. The mobile balloon device or a portion of the inflatable balloon further includes a cylinder with an internal surface that extends longitudinally between and inwardly radially spaced from the balloon legs, which cylinder has a perimeter size throughout that is greater than the catheter external surface given perimeter size adequate to allow sliding longitudinal movement between the catheter and the mobile balloon device. The mobile balloon device further includes at least one radiation dose delivery tube that is positioned, for example by inflation of the balloon with the inflation fluid, to a strategic radiation dose delivery location for brachytherapy.

A further embodiment or aspect concerns a brachytherapy tandem and mobile balloon device system in which a tandem has a distal section and a proximal section having a longitudinally oriented external surface of a given parameter size. A mobile balloon device includes an inflatable balloon having a proximal end portion with a proximal leg, a distal end portion with a distal leg, and the mobile balloon device has an enclosed inner volume structured to receive and securely confine an inflation fluid, the enclosed inner volume being defined fully or partially by the inflatable balloon. The mobile balloon device or a portion of the inflatable balloon further includes an internal surface defining a further portion of the enclosed inner volume, the internal surface having an internal surface perimeter size larger than the tandem external surface perimeter size and adequate to allow sliding longitudinal movement between the tandem and the mobile balloon device. The mobile balloon device has a bulbous inflatable distal end section and further includes at least one radiation dose delivery tube that terminates distally approximately at the distal end surface of the bulbous section and is positioned, for example by inflation of the balloon with the inflation fluid, to a strategic radiation dose delivery location for brachytherapy.

Yet a further embodiment or aspect concerns a brachytherapy tandem and mobile balloon device system in which a tandem has a distal section and a proximal section having a longitudinally oriented external surface of a given parameter size, with the distal and proximal end sections being detachably secured together, and at least the distal end section is made of a material suitable for single-patient use. A mobile balloon device includes an inflatable balloon having a proximal end portion with a proximal leg, a distal end portion with a distal leg, and the mobile balloon device has an enclosed inner volume structured to receive and securely confine an inflation fluid, the enclosed inner volume being defined fully or partially by the inflatable balloon. The mobile balloon device further includes an internal surface or a portion of the inflatable balloon defining a further portion of the enclosed inner volume, the internal surface having an internal surface perimeter size larger than the tandem external surface perimeter size and adequate to allow sliding longitudinal movement between the tandem and the mobile balloon device. The mobile balloon device further includes at least one radiation dose delivery tube that is positioned, for example by inflation of the balloon with the inflation fluid, to a strategic radiation dose delivery location for brachytherapy.

Yet a further embodiment or aspect concerns a brachytherapy tandem and mobile balloon device system in which a tandem has a distal section and a proximal section having a longitudinally oriented external surface of a given parameter size. A mobile balloon device includes an inflatable balloon having a wall with a proximal end portion with a proximal leg, a distal end portion with a distal leg, and the mobile balloon device has an enclosed inner volume structured to receive and securely confine an inflation fluid, the enclosed inner volume being defined partially by the inflatable balloon. The mobile balloon device further includes an internal surface defining a further portion of the enclosed inner volume, the internal surface having an internal surface perimeter size larger than the tandem external surface perimeter size and adequate to allow sliding longitudinal movement between the tandem and the mobile balloon device. The mobile balloon device further includes at least one radiation dose delivery tube that is positioned, for example by inflation of the balloon with the inflation fluid, to a strategic radiation dose delivery location for brachytherapy. The mobile balloon device is associated with one or more of a radiation detector, radiation data receiver, hyperthermia component, and chemical therapy delivery component, or combinations thereof.

Another embodiment or aspect concerns a system and method for intrauterine brachytherapy, comprising providing a catheter such as a tandem sized and structured for intracavitary, intrauterine and/or other body opening or cavity deployment, the catheter having a longitudinal axis, the catheter having a proximal section and a distal section, the proximal section having a longitudinally oriented external surface of a given perimeter size, further providing a mobile balloon device including an inflatable balloon, a proximal end portion with a proximal leg, and a distal end portion with a distal leg, the mobile balloon device has an enclosed inner volume structured to receive and securely confine an inflation fluid, the enclosed inner volume being defined fully or partially by the inflatable balloon and by an internal surface or a portion of the inflatable balloon defining a further portion of the enclosed inner volume, the internal surface having an internal surface perimeter size larger than the tandem external surface perimeter size and adequate to allow sliding longitudinal movement between the catheter and the mobile balloon device, and providing at least one radiation dose delivery tube in association with the inflatable balloon, positioning the tube by inflation of the balloon with an inflation fluid to a strategic radiation dose delivery location for brachytherapy; inserting the catheter distal section within a patient's body opening or cavity, for example such as within the uterus, while a proximal end of the tandem distal section is accessible externally of the patient for example the patient's vagina; sliding the mobile balloon device in a distal direction along the inserted tandem and inflating the inflatable balloon until a strategic location within the uterus or other body cavity or another body opening is reached.

BRIEF DESCRIPTION OF THE DRAWINGS

FIG. 1 is a somewhat schematic illustration of a first embodiment of the distal portion of a brachytherapy system within a typical intrauterine environment; illustrated with a mobile balloon radiation dose delivery device at an initial insertion position; and having internal radiation delivery members;

FIG. 2 is a somewhat schematic illustration of the distal portion of the brachytherapy system within a typical intrauterine environment, illustrated with the FIG. 1 mobile balloon radiation dose delivery device at a substantially fully insertion position and illustrating a low level of inflation;

FIG. 3 is a somewhat schematic illustration of a second embodiment wherein the mobile balloon radiation dose delivery device has multiple radiation delivery members external of the inflatable balloon and shown positioned inwardly or distally and at least partially inflated;

FIG. 4 is a somewhat schematic illustration of a third embodiment with the mobile balloon radiation therapy device positioned fully distally within the vagina and covering all or substantially all of the cervix;

FIG. 5 is a somewhat schematic illustration of a fourth embodiment of the distal portion of a brachytherapy system within a typical intrauterine environment; illustrated with a mobile balloon radiation dose delivery device at a substantially fully inserted position and generally deflated condition;

FIG. 6 is a somewhat schematic illustration of the embodiment of FIG. 5 wherein the mobile balloon radiation dose delivery device is at a substantially fully inflated insertion position, with the distal end face covering the cervix;

FIG. 13 is a longitudinal cross-section generally corresponding to a further embodiment providing a mobile balloon device having a bulbous distal end; and FIG. 14 is a longitudinal cross-section generally corresponding to an additional embodiment providing a mobile balloon device having a bulbous distal end.

DESCRIPTION OF THE ILLUSTRATED EMBODIMENTS

Figure 7:
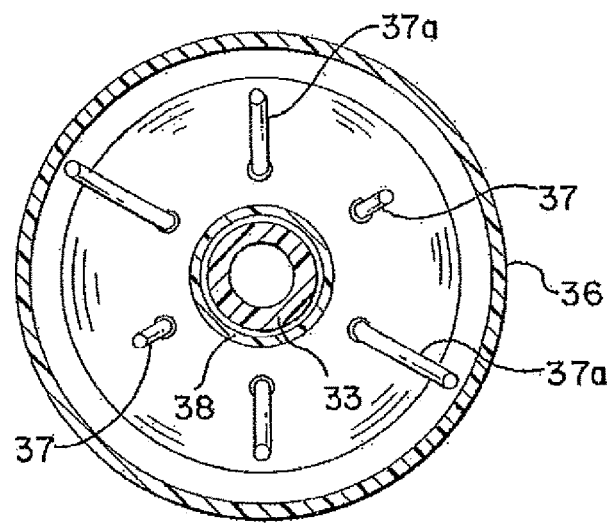
FIG. 7 is a cross-section through the line 7-7 of FIG. 2, illustrating a radiation delivery location internal of the mobile balloon.

The embodiments disclosed herein are exemplary only, and the subject matter described herein may be embodied in various forms. Therefore, specific details described herein are not to be interpreted as limiting the subject matter as defined in the accompanying claims.

FIG. 1 and FIG. 2 illustrate a first embodiment having a catheter taking the form of a tandem generally designated at 31. For purposes of illustration, the catheter device is described herein as a tandem 31. When desired a catheter or tanden can function as a colpostat itself and/or radiation delivery can be by means of the mobile balloon device, generally designated at 32. In some embodiments, one or more ovoids (also referred to as ovoid colpostats generally known in the art and not shown) can be provided. For example, in multiple tandem and ovoid systems, two ovoids are provided in a typical position flanking the tandem 31. In general, tandems can be a length on the order of 20 to 40 cm, depending upon the particular delivery system being used and patient being treated. It will be appreciated that components that supply radiation materials attach to a unit for supplying radioactive materials into the colpostat or delivery channel or tube in order to direct the radioactive treatment material to the desired treatment site within the body of the patient. Details concerning loading of radioactive material to be loaded are not shown and are appreciated and understood by one of skill in this art.

The tandem, generally designated at 31, illustrated in this embodiment is sized and structured for intracavitary or other body opening, natural or surgical, deployment, for example, intrauterine deployment. This illustrated tandem has a proximal section 33 and a distal section 34. In the embodiment illustrated in FIGS. 1 and 2, the proximal and distal sections are detachably secured to each other. Attachment is achieved according to any suitable approach or structure. For example, the distal end of the proximal section 33 and/or the proximal end of the distal section 34 typically include respective mating components that are complementary with each other in that they attach to one another in a secure manner while they also detach from one another when desired and without excessive detachment force required. These attachment components serve to assemble the tandem 31 into a cohesive unit that achieves functions of unitary tandems of other embodiments, but with additional functions described herein.

When the proximal and distal sections of the tandem 31 are detachably connected together, the distal end section 34 is intended for single-patient brachytherapy use. This detachable distal section is sized and shaped for secure long-term implantation within a single patient during multiple radiation doses, as well as during interim time periods between radiation doses during a regimen of brachytherapy treatments. This detachable distal section can be made of a material intended for disposal after completion of a patient treatment regimen, and thus same need not be capable of being cleaned and sterilized multiple times. The basic concept of this detachable distal section 36 is that it remains in place and implanted within a patient during active brachytherapy treatment and during those down times or recovery times between brachytherapy treatments of a multiple-treatment brachytherapy plan or regimen.

The proximal section 33 of detachably connected tandem 31 can be made of a material similar to that of the distal section or same can be made of a durable material typically used for generally known tandems and brachytherapy equipment and procedures or otherwise determined to be suitable for tandems not having detachable features noted herein. Such a typical tandem is made of a metal, for example, stainless steel or other materials suitable for internal medical device multiple-time use, such as certain polymeric materials having the ability to maintain their desirable characteristics during harsh cleaning and sterilization conditions. Tandems tend to exhibit rigidity characteristics adequate to achieve known tandem functions. The typical tandem material is adequate to provide structural support and overall placement location for other components such as the mobile balloon device disclosed herein and/or ovoid colpostats during a brachytherapy procedure. The proximal section 33 of the catheter or tandem 31 is most advantageously structured when made of a material that can withstand multiple cleanings, disinfectings and sterilization procedures. These are intended for multiple-time usage and typically for multiple patients.

The mobile balloon device 32 is slidable along the catheter or tandem, especially along its proximal section such that the device 32 is guided into and out of the body cavity, vaginal cavity 35 in this illustration. Its mobility allows the medical professional to properly place the radiation delivery site or sites of the mobile balloon device where needed according to the radiation treatment regimen for the particular patient. This illustrated mobile balloon device 32 comprises an inflatable balloon 36 and one or more radiation dose delivery tubes 37, as well as an internal surface that accommodates the mobility of the balloon device 32 with respect to the tandem 31. The internal surface can take the form of one or more internal collars 38.

Figure 8:
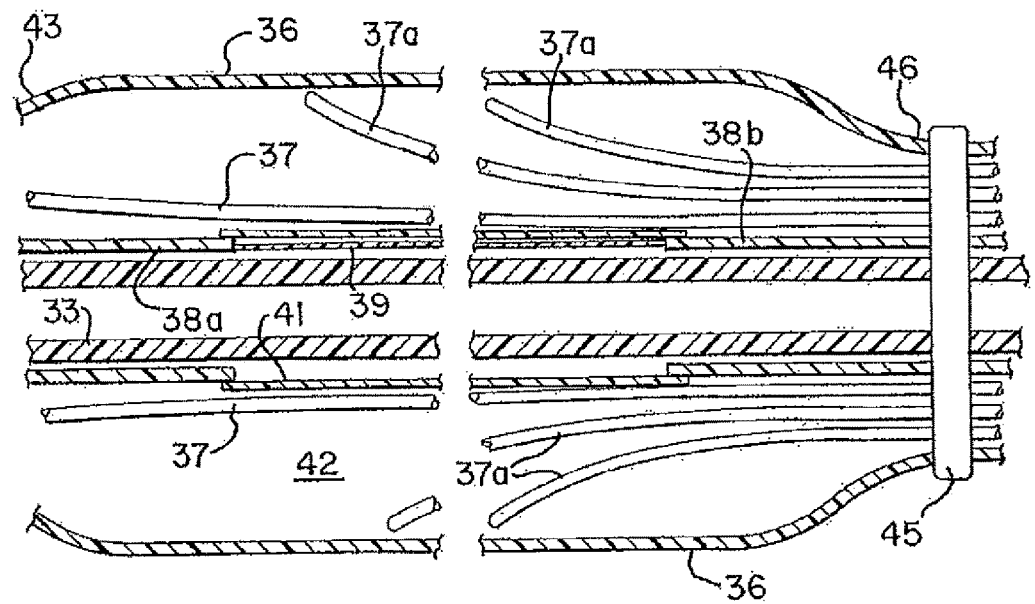
FIG. 8 is a longitudinal cross-section generally corresponding to the embodiment of FIG. 2 having a plurality of internal radiation delivery members.
Figure 9:
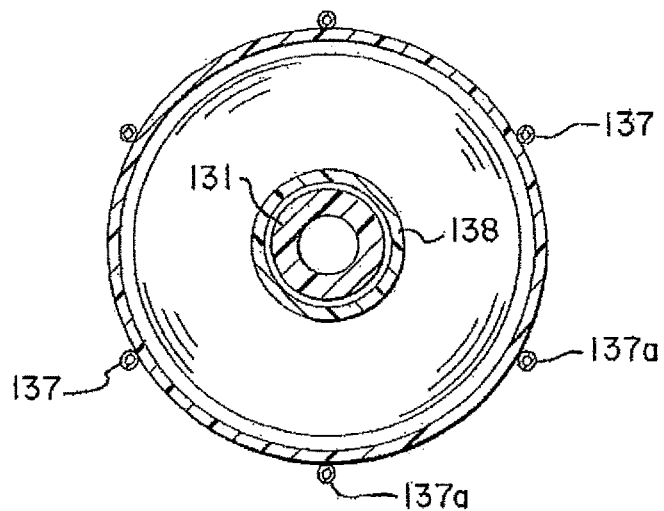
FIG. 9 is a cross-sectional view along the line 9-9 of FIG. 4, illustrating an embodiment with the radiation delivery location within the wall of the mobile inflatable balloon.

In some embodiments, two or more collars can be provided, for example one at either end of the mobile balloon device, such as collars 38a and 38b shown in FIG. 8. When desired, a link 39 can join collars to maintain spacing between the collars and enhance stability of the device during storage and use. Multiple such links can be incorporated. However, for most embodiments, the link approach can require a circumferential seal 41 to maintain an enclosed inner volume 42 of the inflatable balloon that remains sealed during in inflation and deflation use. A simpler alternative approach extends the collar for the full length of the mobile balloon device, taking the form of an internal cylinder, which is illustrated in other embodiments herein.

Whatever the exact structure of the internal surface of the mobile balloon device, the internal surface has a perimeter size, typically a circumference size that is slightly larger than the outside perimeter, e.g. circumference, of the catheter or tandem shaft over which the mobile balloon device is positioned and slides longitudinally during use. The exact dimensional difference between the catheter or tandem external surface perimeter and the internal surface perimeter of the mobile balloon device will depend on the materials of the components that are slidable with respect to each other. A surface interface exhibiting a low coefficient of friction will, all other details being the same, allow a smaller dimensional difference than respective surfaces that do not move as easily with respect to each other. Typical spacing is between about 0.2 mm and about 5 mm, or between about 0.3 and about 4 mm, or between about 0.5 mm and about 2 mm.

In this embodiment, the one or more radiation delivery tubes 37 are inside of the enclosed inner volume of the inflatable balloon 36. Usually, at least one of the tubes 37 extends to or is closely spaced from the distal end portion 43 of the inflatable balloon 36 to enhance radiation dosing at the distal end, which is especially desirable for cervical cancer treatment regimens which can be important when the distal section of the tandem is positioned within the uterus 44. One or more optional radiation delivery tubes 37a can be included, as generally illustrated in FIGS. 2, 7 and 8, should there be a need to treat less remote body locations, e.g. within the vaginal cavity 35.

With the radiation delivery tube or tubes 37, and optional delivery tubes 37a when provided, within the enclosed inner volume of the inflatable balloon 36, in order to maintain the volume in a sealed state, a proximal end plug 45 provides a sealed pass-through for each radiation delivery tube so same can connect with the radiation media supply source. Also in sealed engagement with the end plug 45 are the outer and inner components of the enclosed inner volume, typically the inflatable balloon 36 at its proximal end portion and the internal surface component such as collar 38b or a full-length cylinder 38. A typical inflatable balloon has a proximal leg 46 and a distal leg 47. It is the proximal leg area that is secured to the end plug 45. The distal leg 47 can be secured to the internal collar 38 or 38a, for example.

Concerning multi-component catheters or tandems having a proximal section detachably secured to a distal section, an attachment arrangement 48 is included for secure assembly and easy disassembly. For example, a detachable distal section 34 has a length on the order of 4 cm, 6 cm, 8 cm or 10 cm for an intracervical plastic applicator for uterine placemen, which different lengths of detachable distal section components are provided in order to accommodate different depths of the uterine cavity and cervix locations. A typical detachable proximal section will have a length ranging between about 26 cm and about 34 cm. Somewhat similarly, the mobile balloon device is advantageously provided in different sizes, for example small, medium and large, to accommodate different sizes and shapes of volumes or body cavities to be used in an intended treatment regimen, such as uterine cavities. Examples of attachment arrangements (not shown) include a receptor component, which can be radiopaque and/or metallic or made of metal, one or more projecting components (with or without stepped-down portions), one or more passageways (with or without stepped-down portions), one or more passageways and corresponding receptor components, and complementary interfering elements. These types of features help to prevent unintended detachment between the proximal and distal sections of the tandem assembly. Examples of complementary interfering paired elements (not shown) are threads, indents and detents, snap rings and annular elements.

Concerning arrangements that combine one or more ovoids with the catheter or tandem, an ovoid colpostat (not shown) can include a proximal end portion by which radioactive material is added thereto by communication with dispensing equipment (not shown) familiar to one of skill in this art. In a typical treatment protocol, the radioactive material is delivered to the internal distal delivery location. Often during treatment, this distal delivery location is for treating a diseased cervix or fornix, for example, which can be in combination with tandem-based treatment discussed herein. Depending upon the treatment plan in place, it can be important to include one or more shielding elements (not shown), typically made of lead, tungsten or other radiation-blocking material. Shielding elements also can provide a stand-off function to increase spacing between the internal distal delivery location and a portion of the body that is not to be subjected to treatment. Stand-off functions can be provided by solid, pliable or inflatable components such as balloons to protect such body portions such as the bladder and rectum. When stand-offs are provided in the form of a balloon or balloons, they typically are positioned for use in pushing away rectal tissue. Balloon inflation typically is carried out by passing saline solution or gas such as air or nitrogen through a conduit to the balloon from a source of inflation fluid (not shown).

In addition, a detector 49 is on or associated with the mobile balloon device 32, or the other mobile balloon devices herein in order to detect and measure in vivo dosing and radiation. If desired, "real time" detection, measurement, observation and/or recordation of radiation data can proceed. For example, a detector is placed in an area closely positioned with respect to one or more of the distal end of a radiation delivery tube 37. Transmission of the detector data can be by a wireless system, or a transmission wire or lead 51 can be used for data transmission to a data receptor (not shown). A typical detector is a microdiode. Multiple detectors can be included that detect radiation at different locations and can have a common lead or separate leads or wireless transmission means to the data receptor. One or more detectors can be permanent or removable and can be positioned internally or externally of the mobile balloon device, including its inflatable balloon and/or its tube joining the inflatable balloon to the fluid supply (not shown). Alternatively, detector and/or lead are positioned within the wall of the tube and/or of the balloon member, rather than outside or inside such walls. The inflatable balloon 36 of this or other embodiments may have radiopaque marking and/or may be radiopaque in whole or in part.

Further, with this and other embodiments herein, when desired a hyperthermia system 52, or multiple hyperthermia systems can be included by which heat can be applied to the cancerous area simultaneously with the radiation treatment or if desired in close association in time and location with the radiation treatment imparted by the colpostat. More specifically, the hyperthermia system includes delivery tubes (not shown) that extend between a target location and a hyperthermia fluid source (not shown) of generally known characteristics and structure, such hyperthermia fluid source being outside of the body. In this illustrative embodiment, at least one hyperthermia delivery system is secured to the mobile balloon device 32, and the target location is in the vicinity of the location at which the colpostat of the radiation delivery tube 37 delivers the radiation, which can be low dose radiation, for example. This system applies heat in this colpostat area and generally adjacent to the radiation delivery site. When desired, an integral hyperthermia treatment administration site is positioned at a specific location that is substantially at the radiation delivery site When all of these features and structures are implemented in a single system, including with all of the embodiments of this disclosure, the advantages of hyperthermia are combined with radiation treatment whereby the target tissue is raised in temperature during, or close in time before or after, radiation treatment, which can enhance the effectiveness of the radiation treatment. In addition, the microdiodes or the like, as described elsewhere herein, provide "real time" in vivo detection and measurement of the radiation delivered, which can assist in tailoring a radiation regimen for the particular patient. Moreover, this detection and measurement is carried out at, or in very close proximity to the, location of the radiation treatment and, when desired, also of the hyperthermia treatment, with the objective of providing an unusually efficient and effective combination of patient treatment features.

Concerning the inflatable balloon 36 same can be used for moving either or both the anterior and posterior regions of the vaginal cavity 35 farther away from the radiation oncology treatment site, such as at the cervix 53. This successfully opens the vaginal cavity at an interior location that is relatively closely spaced from the cervix or other treatment target site. For example, the anterior region of the vaginal cavity can be moved to such an extent that the bladder wall itself is moved away from the radiation source. Also, the inflatable balloon 36 of the mobile balloon device can move the posterior wall of the vaginal cavity to such a degree that a portion of the wall of the rectum is moved away from the radiation source.

Figure 10:
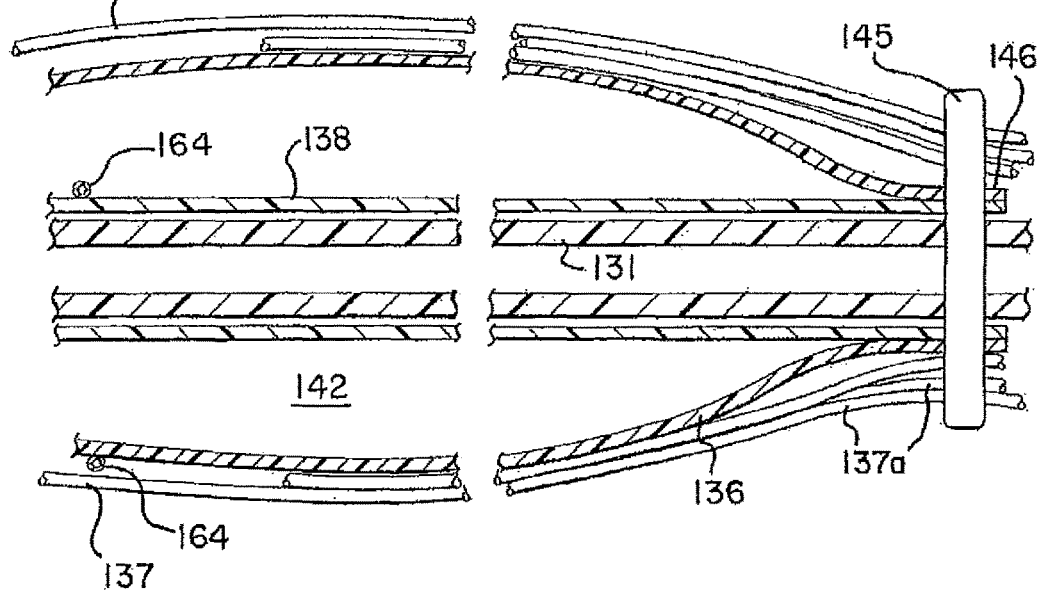
FIG. 10 is a longitudinal cross-section generally corresponding to the embodiment of FIG. 4.

The embodiments of FIGS. 3, 4, 9 and 10 include a mobile balloon device 132 slidable along a catheter or tandem, generally designated at 131 especially along its proximal section such that the device 132 is guided into and out of the body cavity, vaginal cavity 35 in this illustration. Its mobility allows the medical professional to properly place the radiation delivery site or sites of the mobile balloon device where needed according to the radiation treatment regimen for the particular patient. This illustrated mobile balloon device 132 comprises an inflatable balloon 136 and one or more radiation dose delivery tubes 137, as well as an internal surface that accommodates the mobility of the balloon device 132 with respect to the catheter or tandem 131. The internal surface can take the form of one or more internal collars or of an internal cylinder 138. In some embodiments, two or more collars can be provided, for example one at either end of the mobile balloon device, as in the embodiment of FIG. 8. FIG. 10 shows a simpler alternative approach that extends the collar for the full length of the mobile balloon device, taking the form of the internal cylinder 138.

Whatever the exact structure of the internal surface of the mobile balloon device, the internal surface has a perimeter size, typically a circumference size that is slightly larger than the outside perimeter of the catheter or tandem shaft over which the mobile balloon device is positioned and slides longitudinally during use. The exact dimensional difference between the catheter or tandem external surface perimeter and the internal surface perimeter of the mobile balloon device will depend on the materials of the components that are slidable with respect to each other. A surface interface exhibiting a low coefficient of friction will, all other details being the same, allow a smaller dimensional difference than respective surfaces that do not move as easily with respect to each other. Typical spacing is between about 0.5 mm and about 2 mm, or other dimensions noted herein.

In this embodiment, the one or more radiation delivery tubes 137 are outside of the inflatable balloon 136 and the enclosed inner volume 142. Usually, at least one of the tubes 137 extends to or is closely spaced.from the distal end portion 143 of the inflatable balloon 136 to enhance radiation dosing at the distal end, which is especially desirable for cervical cancer treatment regimens which can be important when the distal section of the tandem is positioned within the uterus 44. One or more optional radiation delivery tubes 137*a* can be included, as generally illustrated in FIGS. 3, 4, 9 and 10, should there be a need to treat less remote body locations, e.g. within the vaginal cavity 35.

In an illustrated embodiment, the radiation delivery tube or tubes 137, and when provided optional delivery tubes 137*a*, are outside of the enclosed inner volume 142 of the inflatable balloon 136. In order to assist in controlling placement of the tube or tubes, a proximal end collar 145 can be positioned over the tube or tubes in order to provide a sealed pass-through for each radiation delivery tube so same can connect with the radiation media supply source. A distal end collar 145*a* also can be included to maintain desired placement of the distal ends of at least the tube or tubes 137. A typical inflatable balloon 136 has a proximal leg 146 and a distal leg 147 secured to or sealed with the internal cylinder 138 or collars.

The catheter or tandem can be unitary along the length for placement within the body, or it can be a multi-component tandem as discussed elsewhere herein, having a proximal section detachably secured to a distal section, with an attachment arrangement being included for secure assembly and easy disassembly. For example, this type of device can include a detachable distal section 34 that has a length on the order of 4 cm, 6 cm, 8 cm, etc. Multiple microdiodes 164 and one or more hyperthermia systems 152 can be included.

Figure 11:
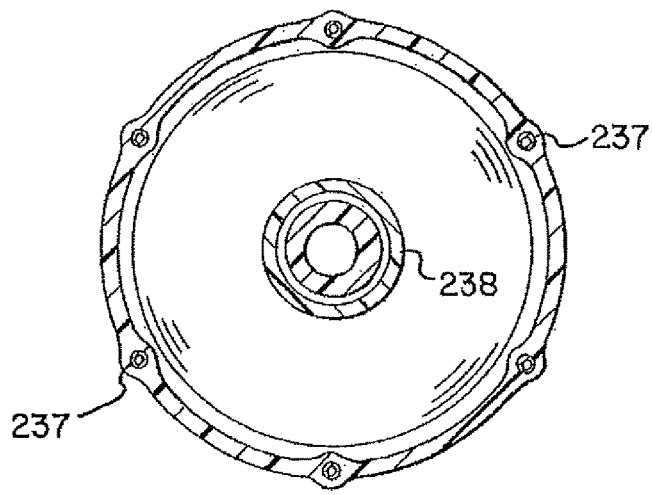
FIG. 11 is a cross-sectional view along the line 11-11 of FIG. 6, illustrating an embodiment with the radiation delivery location internally within the wall of the mobile inflatable balloon.
Figure 12:
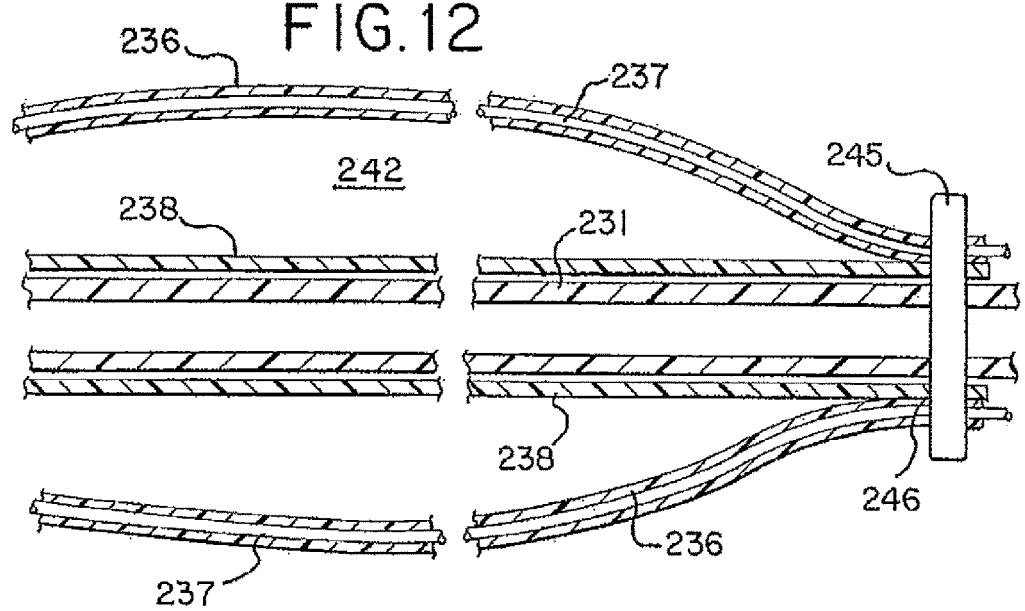
FIG. 12 is a longitudinal cross-section generally corresponding to the embodiment of FIG. 6.

The embodiments of FIGS. 5, 6, 11 and 12 include a mobile balloon device 232 slidable along a catheter or tandem, generally designated at 231 especially along its proximal section such that the device 232 is guided into and out of the body cavity, which is the vaginal cavity 35 in this illustration. As is the case for other embodiments, its mobility allows the medical professional to properly place the radiation delivery site or sites of the mobile balloon device where needed according to the radiation treatment regimen for the particular patient. This illustrated mobile balloon device 232 comprises an inflatable balloon 236 and one or more radiation dose delivery tubes 237, as well as an internal surface, which can be a portion of the inflatable balloon, that accommodates the mobility of the balloon device 232 with respect to the tandem 231. The internal surface can take the form of one or more internal collars or of an internal cylinder 238. In some embodiments, two or more collars can be provided, for example one at either end of the mobile balloon device. The collar embodiment of FIG. 8. FIG. 12 shows a simpler alternative approach that extends the collar for the full length of the mobile balloon device, taking the form of an internal cylinder.

Whatever the exact structure of the internal surface of the mobile balloon device, the internal surface has a perimeter size, typically a circumference size that is slightly larger than the outside perimeter of the catheter or tandem shaft over which the mobile balloon device is positioned and slides longitudinally during use. The exact dimensional difference between the tandem external surface perimeter and the internal surface perimeter of the mobile balloon device will depend on the materials of the components that are slidable with respect to each other. A surface interface exhibiting a low coefficient of friction will, all other details being the same, allow a smaller dimensional difference than respective surfaces that do not move as easily with respect to each other. Typical spacing is between about 0.5 mm and about 2 mm, of other spacing ranges noted herein.

In this embodiment, the one or more radiation delivery tubes 237 are within the thickness of the wall of the inflatable balloon 236 that is outside of the enclosed inner volume 242 of the inflatable balloon 236. Usually, at least one of the tubes 237 extends to or is closely spaced from the distal end portion 243 of the inflatable balloon 236 to enhance radiation dosing at the distal end, which is especially desirable for cervical cancer treatment regimens which can be important when the distal section of the tandem is positioned within the uterus 44. One or more optional radiation delivery tubes 237a can be included, as generally illustrated in FIGS. 5, 6, 11 and 12, and these can, if desired, terminate proximal of the tube or tubes 237, should there be a need to treat less remote body locations, e.g. within the vaginal cavity 35.

The radiation delivery tube or tubes 237, and when provided optional delivery tubes 237a, in this embodiment are outside of the enclosed inner volume of the inflatable balloon 236. The balloon 236 is secured to the internal cylinder 238 at proximal leg 246 of the inflatable balloon. Inflatable balloon 236 also is secured at its distal end portion to the internal cylinder 238. In one embodiment, the distal leg 247 is "tucked under" the distal portion of the inflatable balloon 236, or is continuous with same, so as to provide a more blunt balloon distal end intended for cervix engagement. This structure can facilitate a bulbous distal end feature of some embodiments. The bulbous distal end can be further facilitated by a restrictor 254.

A bulbous distal end 255 of inflatable balloon 236 is shown in a generally deflated condition in FIG. 5 and in an inflated condition in FIG. 6. In FIG. 5, the cylindrical restrictor 254 is illustrated as an embodiment having a necked-down area defined wholly or partly by the restrictor. In FIG. 6, a distal wall surface 256 is shown generally overlying a surface of the cervix 53 to provide engagement and close positioning of radiation source from the delivery tube or tubes 237. FIG. 11 and FIG. 12 show details of an embodiment with two full-length radiation delivery tubes 237 within the balloon wall intended for distal end radiation treatment, near the cervix in this illustrated environment of use. Also illustrated are embodiments having one or more optional radiation delivery tubes 237a, typically being less than the full length of the radiation delivery tubes 237 and intended for treatment of areas proximal of the distal end of the mobile balloon treatment device. The combination of a proximal end securement member 245, the inflatable balloon 236 and the (or its) internal cylinder 238 provide sealed containment for the enclosed inner volume 242 of the mobile balloon device 232.

The catheter or tandem of these embodiments also can be unitary within the body, or it can be a multi-component tandem as discussed elsewhere herein, having a proximal section detachably secured to a distal section, with an attachment arrangement being included for secure assembly and easy disassembly. For example, a detachable distal section 34 has a length on the order of 4 cm, 6 cm, 8 cm, etc. When of a unitary structure, the catheter or tandem will have a length on the order of the total length of a multi-component embodiment. One or more microdiodes 264 and hyperthermia systems 252 can be included.

FIG. 13 illustrates an embodiment that modifies the FIG. 12 embodiment. This shows two radiation delivery tubes 337 that can join with the mobile balloon device at a location that is within the proximal end and/or proximal leg 346 of the inflatable balloon 336. As illustrated in FIG. 13, the placement of the delivery tube or tubes 337 transitions to the space of the enclosed inner volume 342. However the tube or tubes 337 interact proximally outside of the mobile balloon device with other structure, each has its distal end closely spaced from the distal wall surface 356 of the mobile balloon device 332 to provide an embodiment particularly suitable for blunt enveloping procedures which can be useful for treatment of cervical cancers. A proximal end securement member 345 can be provided to assist in maintaining a sealed enclosed inner volume 342.

The bulbous distal end portion 355 achieves an objective of presenting a relatively flat distal wall end surface 356 for engaging a target treatment area, such as the cervical area and forming a bulbous end shape to embrace same. With radiation deployment at the distal portion of the bulbous distal end portion 355, this structure is especially suitable for targeted treatment that can be maintained according to the regimen prescribed by the medical professionals.

In the illustration of FIG. 13, a cylindrical flange 357 of the bulbous portion 355 of the inflatable balloon 336 provides a turn-around proximally extending flange that is part of the sealed distal end portion of the inflatable balloon. In some embodiments, this is achieved by sealing or otherwise attaching the flange 357 to the internal cylinder 338. In other embodiments, the internal cylinder is formed integrally with the inflatable balloon as shown in FIG. 14. In this illustrated arrangement, the flat distal wall end surface 356, an inner proximal bend 358 and the proximally extending flange are one piece, such as having been integrally formed together, with the internal cylinder 338 and with the remainder of the inflatable balloon 336.

With a view toward providing and/or maintaining the bulbous end and necked-down overall shape of the inflatable balloon of the type shown in FIG. 5, FIG. 6, FIG. 13 and FIG. 14, certain areas can have a thicker wall dimension and/or reduced flexibility when compared with other portions of the mobile balloon device 332. For example, the thicker areas can be present along the internal cylinder 238, 338, the inner proximal bend 358, and the proximal leg 246, 346. Other thicker areas can be in association with the necked-down or reduced diameter section 259, 359 of the mobile balloon device 232, 332.

In this regard, each embodiment can include a cylindrical restrictor, such as that illustrated in FIG. 5 at 254, which restrictor can be a separate component, an assembled component, or integrally manufactured with the inflatable balloon. Typically the restrictor will itself expand with inflation of the mobile balloon device; however, due to its thickness and/or lesser expandability when compared with the rest of the expandable balloon, the expansion, or lack thereof, is such that the necked down and bulbous shape can be maintained if desired. When maintained, the exact shape and relative sizing of the necked-down and/or bulbous can vary during inflation.

A necked-down condition can be enhanced by one or more circumferential ribs 361 that bridge the area between the necked down section 359 and the internal cylinder 238, 338. When provided, the rib or ribs can be pervious to allow the full enclosed inner volume to be inflated and deflated by way of a single source of fluid. Alternatively, the rib or ribs can be impervious, thus providing two independent enclosed inner volumes 342a and 342b. In this particular embodiment, separate pathways are provided for filling individual enclosed inner volumes. Pathway 362 fills or otherwise controls the size of proximal independent enclosed inner volume 342a. Pathway 363 fills or otherwise controls the size of proximal independent enclosed inner volume 342b. Radiation delivery tubes 37, 137, 237, 337 attach to a radiation source such as an HDR source as discussed elsewhere herein. A pathway provides inflation fluid, such as liquid or gas, to each enclosed inner volume. When desired, multiple such lumens can be controlled by the same source of fluid. Separate lumens can be connected to the same source channel so that multiple balloons inflate and deflate in general unison. Or, if desired, separate pathways can be controlled separately to inflate or deflate individual enclosed inner volumes when provided.

The enclosed inner volume of this or other embodiments may have radiopaque marking or may be radiopaque in whole or in part. Alternatively or additionally, the balloons of the various embodiments may include one or more microdiodes 364 attached or other devices or systems to provide "real-time" in vivo measuring of radiation. To this end one or more detectors are provided. While transmission associated with a detector or detectors can be a wireless connection, one or more leads or wires and a data receptor (not shown) can be included. These can be provided at locations on the mobile balloon device to detect radiation at different locations and can have a common lead (allowing for separate data paths) or separate leads to the data receptor.

Also, one or more hyperthermia systems 352 can be included as generally noted herein when desired.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. Intrauterine brachytherapy catheter and mobile balloon device system comprising:
    a catheter sized and structured for intracavitary and intrauterine deployment, the catheter having a longitudinal axis, the catheter having a proximal section and a distal section, the proximal section having a longitudinally oriented external surface of a given perimeter size;
    a mobile balloon device including an inflatable balloon having a wall with a wall thickness, a proximal end portion with a proximal leg, and a distal end portion with a distal flange having a distal edge;
    the mobile balloon device has an enclosed inner volume independent of the catheter and that is structured to receive and securely confine an inflation fluid, the enclosed inner volume being defined partially by the inflatable balloon;
    the mobile balloon device further includes an internal cylinder having an external surface defining a further portion of the enclosed inner volume, the internal cylinder having an internal surface of an internal surface perimeter size larger than the catheter external surface perimeter size, wherein a structural relationship between the catheter and the internal cylinder allows sliding longitudinal and rotational movement between the catheter and the internal cylinder;
    each of the proximal leg and the distal flange is unsecured to the catheter, and the distal flange is secured to or is coextensive with the internal cylinder;
    the mobile balloon device further includes at least one radiation dose delivery tube that is positioned, by inflation of the balloon with the inflation fluid, to a strategic radiation dose delivery location for brachytherapy; and
    the distal end portion of the inflatable balloon is an inflatable bulbous distal end, whereby upon inflation the bulbous distal end forms a flat distal end ring that radiates outwardly from the distal edge of the distal flange and is substantially perpendicular to the catheter longitudinal axis, wherein the flat distal end ring engages and lies flat against the cervix in use, and the distal flange of the inflatable balloon does not extend distally of the flat distal end ring; and
    the inflatable balloon further includes a necked-down circumferential restrictor substantially perpendicular to the catheter longitudinal axis and proximal of the inflatable bulbous distal end, thereby dividing the inflatable balloon into an inflatable distal end volume and an inflatable proximal balloon end volume.

2. The system in accordance with claim 1, wherein the at least one radiation delivery tube is positioned within the inflatable balloon.

3. The system in accordance with claim 2, further including a proximal end plug through which the at least one radiation delivery tube passes out of the mobile balloon device, and the plug seals the proximal end portion of the inflatable balloon to further define the enclosed inner volume.

4. The system in accordance with claim 3, further including more than one radiation delivery tube, and wherein the plug has a plurality of openings through which the more than one radiation delivery tubes respectively pass while the plug maintains the enclosed inner volume.

5. The system in accordance with claim 1, wherein the at least one radiation delivery tube is positioned generally along an outside surface of the inflatable balloon.

6. The system in accordance with claim 5, further including a proximal end collar that is external of the inflatable balloon proximal leg, the proximal end collar extends over a portion of and confines the at least one radiation delivery tube while allowing passage of the at least one radiation delivery tube out of the mobile balloon device.

7. The system in accordance with claim 6, further including a distal end collar that is external of the inflatable balloon distal flange, and the distal end collar extends over a portion of and confines a distal portion of the at least one radiation delivery tube.

8. The system in accordance with claim 1, wherein a length of the at least one radiation delivery tube is positioned within the wall of the inflatable balloon, while a proximal length of the at least one radiation delivery tube extends proximally out of the mobile balloon device system.

9. The system in accordance with claim 1, wherein the at least one radiation delivery tube extends to a distal end location of the mobile balloon device system, thereby directing radiation delivery to a patient cervix.

10. The system in accordance with claim 9, further including at least one additional radiation delivery tube, and the at least one additional radiation delivery tube extends to a location that is proximal of the distal end location.

11. The system in accordance with claim 1, wherein the internal surface of the internal cylinder extends longitudinally between and is inwardly radially spaced from the distal flange and the proximal leg of the inflatable balloon, and the internal cylinder has a perimeter size throughout no less than the internal surface perimeter size.

12. The system in accordance with claim 1, wherein the inflatable bulbous distal end has an inflated first circumference, the necked-down circumferential restrictor is between the inflatable bulbous distal end and the inflatable proximal balloon end, and the necked-down circumferential restrictor is of a second circumference, the second circumference being less than the inflated first circumference, and the at least one radiation delivery tube terminates distally approximately at the flat distal end ring, thereby directing radiation delivery to a patient target treatment area.

13. The system in accordance with claim 12, wherein the at least one radiation delivery tube engages the distal end ring of the bulbous distal end.

14. The system in accordance with claim 1, wherein the inflatable balloon and the internal cylinder are separately manufactured components assembled together.

15. The system in accordance with claim 1, wherein the catheter distal section and proximal section are detachably secured to each other;

the distal section of the catheter is made of material suitable for single-patient brachytherapy use, and the proximal section is made of durable material suitable for multiple-patient brachytherapy use;

wherein a proximal end portion of the distal section of the catheter is sized, shaped, and structured to be attachable to and detachable from a distal end portion of the proximal section of the catheter.

16. The system in accordance with claim 15, wherein the distal section is sized and shaped for secure long-term implantation within a single patient between and during multiple oncology doses.

17. The system in accordance with claim 1, wherein said mobile balloon device includes operative components selected from the group consisting of at least one radiation detector and a radiation data receiver; a delivery location generally adjacent to a location along the inflatable balloon, the delivery location being for thermal or chemical therapy delivery; and a hyperthermia system having a thermal delivery location generally adjacent to a radiation delivery location of the mobile balloon device.

18. The system in accordance with claim 1, wherein the distal flange of the inflatable balloon extends proximally of the flat distal end ring and is spaced diametrically inwardly of the inflatable balloon.

19. The system in accordance with claim 1, wherein the necked-down circumferential restrictor includes a rib molded integrally with the balloon.

20. The system in accordance with claim 1, wherein the necked-down circumferential restrictor is secured to the catheter and isolates the inflatable distal end volume from the inflatable proximal end volume, and a first inflation pathway allows inflation of the inflatable distal end volume, and a second inflation pathway allows inflation of the inflatable proximal end volume.

21. A brachytherapy catheter and mobile balloon device system comprising:

a catheter sized and structured for brachytherapy deployment within a patient, the catheter having a longitudinal axis, the catheter having a proximal section and a distal section, the proximal section having a longitudinally oriented external surface of a given perimeter size;

a mobile balloon device including an inflatable balloon section having a proximal end portion with a proximal leg, and a distal end portion with a distal flange having a distal edge;

the mobile balloon device has an enclosed inner volume independent of the catheter and that is structured to receive and securely confine an inflation fluid, the enclosed inner volume being defined partially by the inflatable balloon section;

the mobile balloon device further includes a non-inflatable internal cylinder having an external surface defining a further portion of the enclosed inner volume, the internal cylinder having an internal surface perimeter size larger than the catheter external surface perimeter size, wherein a structural relationship between the catheter and the internal cylinder allows sliding longitudinal and rotational movement between the catheter and the internal cylinder;

each of the proximal leg and the distal flange is unsecured to the catheter, and the distal flange is secured to or is coextensive with the internal cylinder;

the mobile balloon device further includes at least one radiation dose delivery tube that is positioned, by inflation of the balloon with the inflation fluid, to a strategic radiation dose delivery location for brachytherapy;

the distal end portion of the inflatable balloon has an inflatable bulbous distal end, whereby upon inflation the bulbous distal end forms a flat distal end ring that radiates outwardly from the distal edge of the distal flange and is substantially perpendicular to the catheter longitudinal axis, wherein the flat distal end ring engages and lies flat against the cervix in use, and the distal flange of the inflatable balloon does not extend distally of the flat distal end ring; and the inflatable balloon has a first circumference, the inflatable balloon further including a necked-down circumferential restrictor substantially perpendicular to the catheter longitudinal axis and proximal of the inflatable bulbous distal end, thereby dividing the inflatable balloon into an inflatable distal end volume and an inflatable proximal end volume, the necked-down circumferential restrictor is of a second circumference, the second circumference being less than the first circumference, and the necked-down circumferential area is unsecured to the catheter.

22. The system in accordance with claim 21, wherein the distal flange of the inflatable balloon extends proximally of the flat distal end ring and is spaced diametrically inwardly of the inflatable balloon, and the at least one radiation delivery tube terminates distally approximately at the flat distal end ring, thereby directing radiation delivery to a patient target treatment area.

23. The system in accordance with claim 21, wherein the necked-down circumferential restrictor includes a rib molded integrally with the balloon.

24. An intrauterine brachytherapy method, comprising:
providing a tandem sized and structured for intracavitary or intrauterine deployment, the tandem having a longitudinal axis, the tandem having a proximal section and a distal section, the proximal section having a longitudinally oriented external surface of a given perimeter size;
providing a mobile balloon device including an inflatable balloon with a proximal end portion with a proximal leg, and a distal end portion with a distal flange, the inflatable balloon has an inflatable bulbous distal end, the mobile balloon device has an enclosed inner volume independent of the catheter and that is structured to receive and securely confine an inflation fluid, the enclosed inner volume being defined by the inflatable balloon and an internal cylinder having an external surface of the mobile balloon device, the internal cylinder having an internal surface of an internal surface perimeter size larger than the tandem external surface perimeter size, the proximal leg and distal flange are unsecured to the tandem and the distal flange is secured to or is coextensive with the internal cylinder to allow sliding longitudinal movement and rotational movement between the tandem and the mobile balloon device, and the mobile balloon device further includes at least one radiation dose delivery tube that is positioned to a strategic radiation dose delivery location for brachytherapy;
inserting the tandem distal section within a patient's uterus, while a proximal end of the tandem distal section is accessible externally of the patient's vagina;
sliding the mobile balloon device in a distal direction along the inserted tandem, and if necessary rotating the mobile balloon device relative to the inserted tandem until a strategic location within the uterus is reached;
inflating and positioning the inflatable balloon thereby forming from the bulbous distal end a distal end surface flat distal end ring substantially perpendicular to the tandem longitudinal axis, thereby engaging and lying flat against a cervix of a patient, the inflating including restricting inflation at a necked-down circumferential restrictor proximal of the bulbous distal end, the at least one radiation delivery tube positioned for brachytherapy at the patient target treatment area; and
conducting a round of brachytherapy through the at least one radiation delivery tube, thereby directing radiation delivery to the patient target treatment area.

25. The method in accordance with claim 24, further including, after said conducting of a round of brachytherapy, detaching the tandem proximal section from the tandem distal section while retaining the tandem distal section at a deployed location; and subsequently attaching the tandem proximal section to the retained tandem distal section, followed by a further round of brachytherapy.

26. The method in accordance with claim 24, further including, prior to said conducting of a round of brachytherapy, attaching the tandem proximal section to the tandem distal section while the tandem distal section is at a deployed location; and subsequently conducting the round of brachytherapy.

* * * * *